United States Patent
Rosinko

(10) Patent No.: US 11,638,781 B2
(45) Date of Patent: May 2, 2023

(54) SYSTEM AND METHOD FOR SWITCHING BETWEEN CLOSED LOOP AND OPEN LOOP CONTROL OF AN AMBULATORY INFUSION PUMP

(71) Applicant: Tandem Diabetes Care, Inc., San Diego, CA (US)

(72) Inventor: Michael J. Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 700 days.

(21) Appl. No.: 16/791,129

(22) Filed: Feb. 14, 2020

(65) Prior Publication Data

US 2020/0179603 A1    Jun. 11, 2020

Related U.S. Application Data

(63) Continuation of application No. 15/394,066, filed on Dec. 29, 2016, now Pat. No. 10,569,016.
(Continued)

(51) Int. Cl.
  *A61M 5/172*    (2006.01)
  *A61M 5/142*    (2006.01)

(52) U.S. Cl.
  CPC ...... *A61M 5/1723* (2013.01); *A61M 5/14244* (2013.01); *A61M 2205/3553* (2013.01);
(Continued)

(58) Field of Classification Search
  CPC ............ A61M 5/1723; A61M 5/14244; A61M 2205/702; A61M 2205/52;
(Continued)

(56) References Cited

U.S. PATENT DOCUMENTS

| 675,881 A | 6/1901 | Cassullo |
| 2,462,596 A | 2/1949 | Bent |

(Continued)

FOREIGN PATENT DOCUMENTS

| DE | 399065 C | 7/1924 |
| DE | 4407005 C1 | 3/1995 |

(Continued)

OTHER PUBLICATIONS

Application and File History for U.S. Appl. No. 15/394,066, filed Dec. 29, 2016, inventor Rosinko.
(Continued)

*Primary Examiner* — Nathan R Price
*Assistant Examiner* — Anh Bui
(74) *Attorney, Agent, or Firm* — Patterson Thuente IP

(57) ABSTRACT

An infusion pump system providing therapy to a patient in a closed-loop or semi-closed loop mode can safely automatically revert to open-loop therapy. The system stores a default open-loop basal rate profile in memory. The system also continually tracks the insulin on board for the patient over a plurality of closed-loop therapy intervals. When an error or event occurs requiring reversion to open-loop therapy, the system automatically provides therapy according to the open-loop basal rate profile and the tracked insulin on board amount.

20 Claims, 6 Drawing Sheets

Related U.S. Application Data

(60) Provisional application No. 62/272,255, filed on Dec. 29, 2015.

(52) U.S. Cl.
CPC .............. *A61M 2205/3569* (2013.01); *A61M 2205/3584* (2013.01); *A61M 2205/3592* (2013.01); *A61M 2205/505* (2013.01); *A61M 2205/52* (2013.01); *A61M 2205/702* (2013.01); *A61M 2230/005* (2013.01); *A61M 2230/201* (2013.01)

(58) Field of Classification Search
CPC .. A61M 2205/3553; A61M 2205/3569; A61M 2205/3584; A61M 2205/3592; A61M 2230/201; A61M 2230/005
See application file for complete search history.

(56) References Cited

U.S. PATENT DOCUMENTS

| | | |
|---|---|---|
| 2,629,376 A | 2/1953 | Pierre et al. |
| 2,691,542 A | 10/1954 | Chenoweth |
| 3,059,639 A | 10/1962 | Blackman et al. |
| 4,392,849 A | 7/1983 | Petre et al. |
| 4,393,365 A | 7/1983 | Kondo et al. |
| 4,475,901 A | 10/1984 | Kraegen et al. |
| 5,000,664 A | 3/1991 | Lawless et al. |
| 5,050,612 A | 9/1991 | Matsumura |
| 5,122,362 A | 6/1992 | Phillips et al. |
| 5,153,827 A | 10/1992 | Coutre et al. |
| 5,181,910 A | 1/1993 | Scanlon |
| 5,207,666 A | 5/1993 | Idriss et al. |
| 5,219,330 A | 6/1993 | Bollish et al. |
| 5,311,175 A | 5/1994 | Waldman |
| 5,338,157 A | 8/1994 | Blomquist |
| 5,364,346 A | 11/1994 | Schrezenmeir |
| 5,368,562 A | 11/1994 | Blomquist et al. |
| 5,376,070 A | 12/1994 | Purvis et al. |
| 5,389,078 A | 2/1995 | Zalesky et al. |
| 5,395,326 A | 3/1995 | Haber et al. |
| 5,482,446 A | 1/1996 | Williamson et al. |
| 5,485,408 A | 1/1996 | Blomquist |
| 5,551,850 A | 9/1996 | Williamson et al. |
| 5,558,638 A | 9/1996 | Evers et al. |
| 5,569,186 A | 10/1996 | Lord et al. |
| 5,658,250 A | 8/1997 | Blomquist et al. |
| 5,658,252 A | 8/1997 | Johnson |
| 5,665,065 A | 9/1997 | Colman et al. |
| 5,669,877 A | 9/1997 | Blomquist |
| 5,674,240 A | 10/1997 | Bonutti et al. |
| 5,681,285 A | 10/1997 | Ford et al. |
| 5,685,844 A | 11/1997 | Marttila |
| 5,695,473 A | 12/1997 | Olsen |
| 5,713,856 A | 2/1998 | Eggers et al. |
| 5,745,378 A | 4/1998 | Barker et al. |
| 5,782,805 A | 7/1998 | Meinzer et al. |
| 5,800,420 A | 9/1998 | Gross et al. |
| 5,807,375 A | 9/1998 | Gross et al. |
| 5,810,771 A | 9/1998 | Blomquist |
| 5,814,015 A | 9/1998 | Gargano et al. |
| 5,820,622 A | 10/1998 | Gross et al. |
| 5,822,715 A | 10/1998 | Worthington et al. |
| 5,876,370 A | 3/1999 | Blomquist |
| 5,879,143 A | 3/1999 | Cote et al. |
| 5,885,211 A | 3/1999 | Eppstein et al. |
| 5,935,099 A | 8/1999 | Peterson et al. |
| 5,935,106 A | 8/1999 | Olsen |
| 5,960,403 A | 9/1999 | Brown |
| 6,023,629 A | 2/2000 | Tamada |
| 6,024,539 A | 2/2000 | Blomquist |
| 6,077,055 A | 6/2000 | Vilks |
| 6,122,536 A | 9/2000 | Sun et al. |
| 6,142,939 A | 11/2000 | Eppstein et al. |
| 6,175,752 B1 | 1/2001 | Say et al. |
| 6,233,471 B1 | 5/2001 | Berner et al. |
| 6,241,704 B1 | 6/2001 | Peterson et al. |
| 6,248,057 B1 | 6/2001 | Mavity et al. |
| 6,248,067 B1 | 6/2001 | Causey, III et al. |
| 6,249,717 B1 | 6/2001 | Nicholson et al. |
| 6,255,781 B1 | 7/2001 | Tsumura |
| 6,272,364 B1 | 8/2001 | Kurnik |
| 6,298,254 B2 | 10/2001 | Tamada |
| 6,306,420 B1 | 10/2001 | Cheikh |
| 6,368,272 B1 | 4/2002 | Porumbescu |
| 6,379,301 B1 | 4/2002 | Worthington et al. |
| 6,422,057 B1 | 7/2002 | Anderson |
| 6,427,088 B1 | 7/2002 | Bowman, IV et al. |
| 6,475,180 B2 | 11/2002 | Peterson et al. |
| 6,505,059 B1 | 1/2003 | Kollias et al. |
| 6,517,482 B1 | 2/2003 | Elden et al. |
| 6,535,714 B2 | 3/2003 | Melker et al. |
| 6,539,250 B1 | 3/2003 | Bettinger |
| 6,544,212 B2 | 4/2003 | Galley et al. |
| 6,544,229 B1 | 4/2003 | Danby et al. |
| 6,546,269 B1 | 4/2003 | Kurnik |
| 6,551,276 B1 | 4/2003 | Mann et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,565,509 B1 | 5/2003 | Say et al. |
| 6,571,128 B2 | 5/2003 | Lebel et al. |
| 6,577,899 B2 | 6/2003 | Lebel et al. |
| 6,582,366 B1 | 6/2003 | Porumbescu |
| 6,585,644 B2 | 7/2003 | Lebel et al. |
| 6,595,919 B2 | 7/2003 | Berner et al. |
| 6,623,698 B2 | 9/2003 | Kuo |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,114 B1 | 12/2003 | Poulsen et al. |
| 6,659,948 B2 | 12/2003 | Lebel et al. |
| 6,659,978 B1 | 12/2003 | Kasuga et al. |
| 6,668,196 B1 | 12/2003 | Villegas et al. |
| 6,687,522 B2 | 2/2004 | Tamada |
| 6,687,546 B2 | 2/2004 | Lebel et al. |
| 6,694,191 B2 | 2/2004 | Starkweather et al. |
| 6,733,446 B2 | 5/2004 | Lebel et al. |
| 6,740,072 B2 | 5/2004 | Starkweather et al. |
| 6,740,075 B2 | 5/2004 | Lebel et al. |
| 6,744,350 B2 | 6/2004 | Blomquist |
| 6,771,250 B1 | 8/2004 | Oh |
| 6,773,412 B2 | 8/2004 | O'Mahony et al. |
| 6,790,198 B1 | 9/2004 | White et al. |
| 6,809,633 B2 | 10/2004 | Cern |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,835,175 B1 | 12/2004 | Porumbescu |
| 6,852,104 B2 | 2/2005 | Blomquist |
| 6,862,466 B2 | 3/2005 | Ackerman |
| 6,872,200 B2 | 3/2005 | Mann et al. |
| 6,873,268 B2 | 3/2005 | Lebel et al. |
| 6,880,564 B2 | 4/2005 | Erickson |
| 6,882,940 B2 | 4/2005 | Potts et al. |
| 6,895,263 B2 | 5/2005 | Shin et al. |
| 6,902,905 B2 | 6/2005 | Burson et al. |
| 6,916,159 B2 | 7/2005 | Rush et al. |
| 6,918,542 B2 | 7/2005 | Silverbrook et al. |
| 6,934,220 B1 | 8/2005 | Cruitt et al. |
| 6,936,029 B2 | 8/2005 | Mann et al. |
| 6,950,708 B2 | 9/2005 | Bowman, IV et al. |
| 6,957,655 B2 | 10/2005 | Erickson et al. |
| 6,958,705 B2 | 10/2005 | Lebel et al. |
| 6,966,325 B2 | 11/2005 | Erickson |
| 6,970,742 B2 | 11/2005 | Mann et al. |
| 6,974,437 B2 | 12/2005 | Lebel et al. |
| 6,979,326 B2 | 12/2005 | Mann et al. |

(56) References Cited

U.S. PATENT DOCUMENTS

| | | |
|---|---|---|
| 6,997,920 B2 | 2/2006 | Mann et al. |
| 6,998,387 B1 | 2/2006 | Goke et al. |
| 6,999,854 B2 | 2/2006 | Roth |
| 7,004,928 B2 | 2/2006 | Aceti et al. |
| 7,022,072 B2 | 4/2006 | Fox et al. |
| 7,024,245 B2 | 4/2006 | Lebel et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,073,713 B2 | 7/2006 | Silverbrook et al. |
| 7,083,108 B2 | 8/2006 | Silverbrook et al. |
| 7,092,011 B2 | 8/2006 | Silverbrook et al. |
| 7,097,108 B2 | 8/2006 | Zellner et al. |
| 7,098,803 B2 | 8/2006 | Mann et al. |
| 7,109,878 B2 | 9/2006 | Mann et al. |
| 7,150,741 B2 | 12/2006 | Erickson et al. |
| 7,156,808 B2 | 1/2007 | Quy |
| 7,179,226 B2 | 2/2007 | Crothall et al. |
| 7,181,505 B2 | 2/2007 | Haller et al. |
| 7,183,068 B2 | 2/2007 | Burson et al. |
| 7,187,404 B2 | 3/2007 | Silverbrook et al. |
| 7,201,319 B2 | 4/2007 | Silverbrook et al. |
| 7,204,823 B2 | 4/2007 | Estes et al. |
| 7,231,263 B2 | 6/2007 | Choi |
| 7,234,645 B2 | 6/2007 | Silverbrook et al. |
| 7,247,702 B2 | 7/2007 | Gardner et al. |
| 7,254,782 B1 | 8/2007 | Sherer |
| 7,267,665 B2 | 9/2007 | Steil et al. |
| 7,278,983 B2 | 10/2007 | Ireland et al. |
| 7,282,029 B1 | 10/2007 | Poulsen et al. |
| 7,289,142 B2 | 10/2007 | Silverbrook |
| 7,291,107 B2 | 11/2007 | Hellwig et al. |
| 7,295,867 B2 | 11/2007 | Berner et al. |
| 7,307,245 B2 | 12/2007 | Faries, Jr. et al. |
| 7,320,675 B2 | 1/2008 | Pastore et al. |
| 7,324,012 B2 | 1/2008 | Mann et al. |
| 7,341,577 B2 | 3/2008 | Gill |
| 7,347,819 B2 | 3/2008 | Lebel et al. |
| 7,347,836 B2 | 3/2008 | Peterson et al. |
| 7,354,420 B2 | 4/2008 | Steil et al. |
| 7,362,971 B2 | 4/2008 | Silverbrook et al. |
| 7,369,635 B2 | 5/2008 | Spital et al. |
| 7,373,083 B2 | 5/2008 | Silverbrook et al. |
| 7,377,706 B2 | 5/2008 | Silverbrook et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,446,091 B2 | 11/2008 | Van Den Berghe |
| 7,460,152 B2 | 12/2008 | Silverbrook et al. |
| 7,464,010 B2 | 12/2008 | Yang et al. |
| 7,471,994 B2 | 12/2008 | Ford et al. |
| 7,475,825 B2 | 1/2009 | Silverbrook et al. |
| 7,483,050 B2 | 1/2009 | Silverbrook et al. |
| 7,483,743 B2 | 1/2009 | Mann et al. |
| 7,491,187 B2 | 2/2009 | Van Den Berghe et al. |
| 7,497,827 B2 | 3/2009 | Brister et al. |
| 7,515,060 B2 | 4/2009 | Blomquist |
| 7,524,045 B2 | 4/2009 | Silverbrook et al. |
| 7,534,226 B2 | 5/2009 | Mernoe et al. |
| 7,547,281 B2 | 6/2009 | Hayes et al. |
| 7,553,281 B2 | 6/2009 | Hellwig et al. |
| 7,556,613 B2 | 7/2009 | Wittmann et al. |
| 7,559,926 B1 | 7/2009 | Blischak |
| 7,569,030 B2 | 8/2009 | Lebel et al. |
| 7,588,046 B1 | 9/2009 | Erickson |
| 7,591,801 B2 | 9/2009 | Brauker et al. |
| 7,602,310 B2 | 10/2009 | Mann et al. |
| 7,647,237 B2 | 1/2010 | Malave et al. |
| 7,651,489 B2 | 1/2010 | Estes et al. |
| 7,651,845 B2 | 1/2010 | Doyle, III et al. |
| 7,654,976 B2 | 2/2010 | Peterson et al. |
| 7,674,485 B2 | 3/2010 | Bhaskaran et al. |
| 7,676,519 B2 | 3/2010 | McBride et al. |
| 7,678,071 B2 | 3/2010 | Lebel et al. |
| 7,678,762 B2 | 3/2010 | Green et al. |
| 7,678,763 B2 | 3/2010 | Green et al. |
| 7,687,272 B1 | 3/2010 | Buchwald et al. |
| 7,697,967 B2 | 4/2010 | Stafford |
| 7,704,226 B2 | 4/2010 | Mueller, Jr. et al. |
| 7,708,717 B2 | 5/2010 | Estes et al. |
| 7,711,402 B2 | 5/2010 | Shults et al. |
| 7,715,893 B2 | 5/2010 | Kamath et al. |
| 7,717,903 B2 | 5/2010 | Estes et al. |
| 7,722,536 B2 | 5/2010 | Goodnow |
| 7,734,323 B2 | 6/2010 | Blomquist et al. |
| 7,751,907 B2 | 7/2010 | Blomquist |
| 7,766,829 B2 | 8/2010 | Sloan et al. |
| 7,766,830 B2 | 8/2010 | Fox et al. |
| 7,768,386 B2 | 8/2010 | Hayter et al. |
| 7,768,408 B2 | 8/2010 | Reggiardo et al. |
| 7,774,145 B2 | 8/2010 | Brauker et al. |
| 7,776,030 B2 | 8/2010 | Estes et al. |
| 7,778,680 B2 | 8/2010 | Goode, Jr. et al. |
| 7,785,313 B2 | 8/2010 | Mastrototaro |
| 7,794,426 B2 | 9/2010 | Briones et al. |
| 7,794,427 B2 | 9/2010 | Estes et al. |
| 7,794,428 B2 | 9/2010 | Estes et al. |
| 7,797,028 B2 | 9/2010 | Goode, Jr. et al. |
| 7,801,582 B2 | 9/2010 | Peyser |
| 7,806,853 B2 | 10/2010 | Wittmann et al. |
| 7,806,886 B2 | 10/2010 | Kanderian, Jr. et al. |
| 7,815,602 B2 | 10/2010 | Mann et al. |
| 7,819,843 B2 | 10/2010 | Mann et al. |
| 7,822,455 B2 | 10/2010 | Hoss et al. |
| 7,826,879 B2 | 11/2010 | Hoss et al. |
| 7,828,528 B2 | 11/2010 | Estes et al. |
| 7,831,310 B2 | 11/2010 | Lebel et al. |
| 7,833,196 B2 | 11/2010 | Estes et al. |
| 7,837,647 B2 | 11/2010 | Estes et al. |
| 7,837,651 B2 | 11/2010 | Bishop et al. |
| 7,850,641 B2 | 12/2010 | Lebel et al. |
| 7,860,544 B2 | 12/2010 | Say et al. |
| 7,869,851 B2 | 1/2011 | Hellwig et al. |
| 7,869,853 B1 | 1/2011 | Say et al. |
| 7,875,022 B2 | 1/2011 | Wenger et al. |
| 7,884,729 B2 | 2/2011 | Reggiardo et al. |
| 7,885,699 B2 | 2/2011 | Say et al. |
| 7,887,512 B2 | 2/2011 | Estes et al. |
| 7,890,295 B2 | 2/2011 | Shin et al. |
| 7,892,199 B2 | 2/2011 | Mhatre et al. |
| 7,912,674 B2 | 3/2011 | Killoren Clark et al. |
| 7,914,450 B2 | 3/2011 | Goode, Jr. et al. |
| 7,914,499 B2 | 3/2011 | Gonnelli et al. |
| 7,920,907 B2 | 4/2011 | McGarraugh et al. |
| 7,933,780 B2 | 4/2011 | De La Huerga |
| 7,935,076 B2 | 5/2011 | Estes et al. |
| 7,938,797 B2 | 5/2011 | Estes |
| 7,938,803 B2 | 5/2011 | Mernoe et al. |
| 7,941,200 B2 | 5/2011 | Weinert et al. |
| 7,942,844 B2 | 5/2011 | Moberg et al. |
| 7,946,985 B2 | 5/2011 | Mastrototaro et al. |
| 7,951,114 B2 | 5/2011 | Rush et al. |
| 7,959,598 B2 | 6/2011 | Estes |
| 7,963,946 B2 | 6/2011 | Moubayed et al. |
| 7,967,773 B2 | 6/2011 | Amborn et al. |
| 7,972,296 B2 | 7/2011 | Braig et al. |
| 7,976,492 B2 | 7/2011 | Brauker et al. |
| 7,981,034 B2 | 7/2011 | Jennewine et al. |
| 7,981,084 B2 | 7/2011 | Estes et al. |
| 7,981,102 B2 | 7/2011 | Patel et al. |
| 7,983,745 B2 | 7/2011 | Hatlestad et al. |
| 7,983,759 B2 | 7/2011 | Stahmann et al. |
| 7,985,330 B2 | 7/2011 | Wang et al. |
| 7,988,630 B1 | 8/2011 | Osorio et al. |
| 7,988,849 B2 | 8/2011 | Biewer et al. |
| 7,996,158 B2 | 8/2011 | Hayter et al. |
| 8,005,524 B2 | 8/2011 | Brauker et al. |
| 8,012,119 B2 | 9/2011 | Estes et al. |
| 8,016,783 B2 | 9/2011 | Pastore et al. |
| 8,025,634 B1 | 9/2011 | Moubayed et al. |
| 8,029,459 B2 | 10/2011 | Rush et al. |
| 8,029,460 B2 | 10/2011 | Rush et al. |
| 8,062,249 B2 | 11/2011 | Wilinska et al. |
| 8,066,665 B2 | 11/2011 | Rush et al. |

(56) References Cited

U.S. PATENT DOCUMENTS

| | | |
|---|---|---|
| 8,075,527 B2 | 12/2011 | Rush et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,093,212 B2 | 1/2012 | Gardner et al. |
| 8,105,268 B2 | 1/2012 | Lebel et al. |
| 8,105,279 B2 | 1/2012 | Mernoe et al. |
| 8,109,921 B2 | 2/2012 | Estes et al. |
| 8,114,350 B1 | 2/2012 | Silver et al. |
| 8,118,770 B2 | 2/2012 | Galley et al. |
| 8,119,593 B2 | 2/2012 | Richardson et al. |
| 8,127,046 B2 | 2/2012 | Grant et al. |
| 8,129,429 B2 | 3/2012 | Sporn et al. |
| 8,133,197 B2 | 3/2012 | Blomquist et al. |
| 8,140,275 B2 | 3/2012 | Campbell et al. |
| 8,140,312 B2 | 3/2012 | Hayter et al. |
| 8,147,446 B2 | 4/2012 | Yodfat et al. |
| 8,152,789 B2 | 4/2012 | Starkweather et al. |
| 8,170,721 B2 | 5/2012 | Nickerson |
| 8,177,716 B2 | 5/2012 | Say et al. |
| 8,182,445 B2 | 5/2012 | Moubayed et al. |
| 8,192,394 B2 | 6/2012 | Estes et al. |
| 8,192,395 B2 | 6/2012 | Estes et al. |
| 8,202,267 B2 | 6/2012 | Field et al. |
| 8,204,729 B2 | 6/2012 | Sher |
| 8,206,296 B2 | 6/2012 | Jennewine |
| 8,206,350 B2 | 6/2012 | Mann et al. |
| 8,208,984 B2 | 6/2012 | Blomquist et al. |
| 8,211,062 B2 | 7/2012 | Estes et al. |
| 8,219,222 B2 | 7/2012 | Blomquist |
| 8,221,345 B2 | 7/2012 | Blomquist |
| 8,221,385 B2 | 7/2012 | Estes |
| 8,226,558 B2 | 7/2012 | Say et al. |
| 8,226,891 B2 | 7/2012 | Sloan et al. |
| 8,231,562 B2 | 7/2012 | Buck et al. |
| 8,234,126 B1 | 7/2012 | Estes |
| 8,234,128 B2 | 7/2012 | Martucci et al. |
| 8,237,715 B2 | 8/2012 | Buck et al. |
| 8,246,540 B2 | 8/2012 | Ginsberg |
| 8,250,483 B2 | 8/2012 | Blomquist |
| 8,251,904 B2 | 8/2012 | Zivitz et al. |
| 8,251,906 B2 | 8/2012 | Brauker et al. |
| 8,257,259 B2 | 9/2012 | Brauker et al. |
| 8,257,300 B2 | 9/2012 | Budiman et al. |
| 8,260,630 B2 | 9/2012 | Brown |
| 8,262,617 B2 | 9/2012 | Aeschlimann et al. |
| 8,277,435 B2 | 10/2012 | Estes |
| 8,282,601 B2 | 10/2012 | Mernoe et al. |
| 8,287,454 B2 | 10/2012 | Wolpert et al. |
| 8,287,495 B2 | 10/2012 | Michaud et al. |
| 8,287,514 B2 | 10/2012 | Miller et al. |
| 8,290,562 B2 | 10/2012 | Goode, Jr. et al. |
| 8,298,184 B2 | 10/2012 | DiPerna et al. |
| 8,311,749 B2 | 11/2012 | Brauker et al. |
| 8,323,188 B2 | 12/2012 | Tran |
| 8,328,754 B2 | 12/2012 | Estes et al. |
| 8,343,092 B2 | 1/2013 | Rush et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,348,886 B2 | 1/2013 | Kanderian, Jr. et al. |
| 8,348,923 B2 | 1/2013 | Kanderian, Jr. et al. |
| 8,349,319 B2 | 1/2013 | Schuchman et al. |
| 8,357,091 B2 | 1/2013 | Say et al. |
| 8,369,919 B2 * | 2/2013 | Kamath ............... A61B 5/1495 600/347 |
| 8,372,040 B2 | 2/2013 | Huang et al. |
| 8,376,943 B2 | 2/2013 | Kovach et al. |
| 8,377,031 B2 | 2/2013 | Hayter et al. |
| 8,380,273 B2 | 2/2013 | Say et al. |
| 8,409,131 B2 | 4/2013 | Say et al. |
| 8,414,523 B2 | 4/2013 | Blomquist et al. |
| 8,444,595 B2 | 5/2013 | Brukalo et al. |
| 8,449,523 B2 | 5/2013 | Brukalo et al. |
| 8,451,230 B2 | 5/2013 | Celentano et al. |
| 8,452,953 B2 | 5/2013 | Buck et al. |
| 8,454,510 B2 | 6/2013 | Yodfat et al. |
| 8,454,575 B2 | 6/2013 | Estes et al. |
| 8,454,576 B2 | 6/2013 | Mastrototaro et al. |
| 8,454,581 B2 | 6/2013 | Estes et al. |
| 8,460,231 B2 | 6/2013 | Brauker et al. |
| 8,465,460 B2 | 6/2013 | Yodfat et al. |
| 8,467,980 B2 | 6/2013 | Campbell et al. |
| 8,475,409 B2 | 7/2013 | Javitt |
| 8,486,005 B2 | 7/2013 | Yodfat et al. |
| 8,552,880 B2 | 10/2013 | Kopp et al. |
| 8,562,558 B2 | 10/2013 | Kamath et al. |
| 8,573,027 B2 | 11/2013 | Rosinko et al. |
| 8,579,853 B2 | 11/2013 | Reggiardo et al. |
| 8,650,937 B2 | 2/2014 | Brown |
| 8,657,779 B2 | 2/2014 | Blomquist |
| 8,712,748 B2 | 4/2014 | Thukral et al. |
| 8,718,949 B2 | 5/2014 | Blomquist et al. |
| 8,726,266 B2 | 5/2014 | Kiaie et al. |
| 8,775,877 B2 | 7/2014 | McVey et al. |
| 8,801,657 B2 | 8/2014 | Blomquist et al. |
| 8,882,701 B2 | 11/2014 | DeBelser et al. |
| 8,938,306 B2 | 1/2015 | Lebel et al. |
| 8,986,253 B2 | 3/2015 | DiPerna |
| 8,992,475 B2 | 3/2015 | Mann et al. |
| 9,008,803 B2 | 4/2015 | Blomquist |
| 9,037,254 B2 | 5/2015 | John |
| 9,089,305 B2 | 7/2015 | Hovorka |
| 9,364,679 B2 | 6/2016 | John |
| 9,381,297 B2 | 7/2016 | Brown et al. |
| 9,474,856 B2 | 10/2016 | Blomquist |
| 9,486,171 B2 | 11/2016 | Saint |
| 9,486,578 B2 | 11/2016 | Finan et al. |
| 9,669,160 B2 | 6/2017 | Harris et al. |
| 9,833,177 B2 | 12/2017 | Blomquist |
| 9,867,937 B2 | 1/2018 | Saint et al. |
| 9,867,953 B2 | 6/2018 | Rosinko |
| 10,016,561 B2 | 7/2018 | Saint et al. |
| 10,052,049 B2 | 8/2018 | Blomquist et al. |
| 10,130,766 B1 * | 11/2018 | Bibian ................. A61M 5/145 |
| 10,213,547 B2 | 2/2019 | Rosinko |
| 10,357,606 B2 | 7/2019 | Blomquist et al. |
| 10,357,607 B2 | 7/2019 | Blomquist et al. |
| 10,549,051 B2 | 2/2020 | Rosinko |
| 10,569,016 B2 | 2/2020 | Rosinko |
| 10,864,322 B2 | 12/2020 | Saint et al. |
| 2001/0001144 A1 | 5/2001 | Kapp |
| 2001/0031944 A1 | 10/2001 | Peterson et al. |
| 2001/0037217 A1 | 11/2001 | Abensour et al. |
| 2001/0041831 A1 | 11/2001 | Starkweather et al. |
| 2002/0002326 A1 | 1/2002 | Causey, III et al. |
| 2002/0016568 A1 | 2/2002 | Lebel et al. |
| 2002/0065454 A1 | 5/2002 | Lebel et al. |
| 2002/0072932 A1 | 6/2002 | Swamy |
| 2002/0077852 A1 | 6/2002 | Ford et al. |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0032867 A1 | 2/2003 | Crothall et al. |
| 2003/0036683 A1 | 2/2003 | Kehr et al. |
| 2003/0050621 A1 | 3/2003 | Lebel et al. |
| 2003/0060765 A1 | 3/2003 | Campbell et al. |
| 2003/0065308 A1 | 4/2003 | Lebel et al. |
| 2003/0088238 A1 | 5/2003 | Poulsen et al. |
| 2003/0104982 A1 | 6/2003 | Wittmann et al. |
| 2003/0114836 A1 | 6/2003 | Estes et al. |
| 2003/0130616 A1 | 7/2003 | Steil et al. |
| 2003/0145854 A1 | 8/2003 | Hickle |
| 2003/0159945 A1 | 8/2003 | Miyazaki et al. |
| 2003/0160683 A1 | 8/2003 | Blomquist |
| 2003/0161744 A1 | 8/2003 | Vilks et al. |
| 2003/0163088 A1 | 8/2003 | Blomquist |
| 2003/0163090 A1 | 8/2003 | Blomquist et al. |
| 2003/0163223 A1 | 8/2003 | Blomquist |
| 2003/0163789 A1 | 8/2003 | Blomquist |
| 2003/0199854 A1 | 10/2003 | Kovach et al. |
| 2003/0208113 A1 | 11/2003 | Mault et al. |

(56) References Cited

U.S. PATENT DOCUMENTS

| | | |
|---|---|---|
| 2003/0212364 A1 | 11/2003 | Mann et al. |
| 2003/0212379 A1 | 11/2003 | Bylund et al. |
| 2003/0236489 A1 | 12/2003 | Jacobson et al. |
| 2004/0015102 A1 | 1/2004 | Cummings et al. |
| 2004/0015132 A1 | 1/2004 | Brown |
| 2004/0054263 A1 | 3/2004 | Moerman et al. |
| 2004/0068230 A1 | 4/2004 | Estes et al. |
| 2004/0073095 A1 | 4/2004 | Causey, III et al. |
| 2004/0115067 A1 | 6/2004 | Rush et al. |
| 2004/0122353 A1 | 6/2004 | Shahmirian et al. |
| 2004/0152622 A1 | 8/2004 | Keith et al. |
| 2004/0167464 A1 | 8/2004 | Ireland et al. |
| 2004/0180810 A1 | 9/2004 | Pilarski |
| 2004/0193025 A1 | 9/2004 | Steil et al. |
| 2004/0193090 A1 | 9/2004 | Lebel et al. |
| 2004/0225252 A1 | 11/2004 | Gillespie et al. |
| 2004/0254434 A1 | 12/2004 | Goodnow et al. |
| 2005/0021006 A1 | 1/2005 | Tonnies |
| 2005/0022274 A1 | 1/2005 | Campbell et al. |
| 2005/0027182 A1 | 2/2005 | Siddiqui et al. |
| 2005/0030164 A1 | 2/2005 | Blomquist |
| 2005/0049179 A1 | 3/2005 | Davidson et al. |
| 2005/0050621 A1 | 3/2005 | Thomas |
| 2005/0065464 A1 | 3/2005 | Talbot et al. |
| 2005/0065760 A1 | 3/2005 | Murtfeldt et al. |
| 2005/0081847 A1 | 4/2005 | Lee et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0171513 A1 | 8/2005 | Mann et al. |
| 2005/0182358 A1 | 8/2005 | Veit et al. |
| 2005/0192557 A1 | 9/2005 | Brauker et al. |
| 2005/0197553 A1 | 9/2005 | Cooper |
| 2005/0197621 A1 | 9/2005 | Poulsen et al. |
| 2005/0203349 A1 | 9/2005 | Nanikashvili |
| 2005/0203360 A1 | 9/2005 | Brauker et al. |
| 2005/0228234 A1 | 10/2005 | Yang |
| 2005/0272640 A1 | 12/2005 | Doyle, III et al. |
| 2005/0277872 A1 | 12/2005 | Colby, Jr. et al. |
| 2005/0277912 A1 | 12/2005 | John |
| 2006/0001538 A1 | 1/2006 | Kraft et al. |
| 2006/0001550 A1 | 1/2006 | Mann et al. |
| 2006/0014670 A1 | 1/2006 | Green et al. |
| 2006/0031094 A1 | 2/2006 | Cohen et al. |
| 2006/0047192 A1 | 3/2006 | Hellwig et al. |
| 2006/0047538 A1 | 3/2006 | Condurso et al. |
| 2006/0080059 A1 | 4/2006 | Stupp et al. |
| 2006/0085223 A1 | 4/2006 | Anderson et al. |
| 2006/0093785 A1 | 5/2006 | Hickle |
| 2006/0094985 A1 | 5/2006 | Aceti et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0167345 A1 | 7/2006 | Vespasiani |
| 2006/0173406 A1 | 8/2006 | Hayes et al. |
| 2006/0173444 A1 | 8/2006 | Choy et al. |
| 2006/0202859 A1 | 9/2006 | Mastrototaro et al. |
| 2006/0224109 A1 | 10/2006 | Steil et al. |
| 2006/0253097 A1 | 11/2006 | Braig et al. |
| 2006/0253296 A1 | 11/2006 | Liisberg et al. |
| 2006/0264895 A1 | 11/2006 | Flanders |
| 2006/0271020 A1 | 11/2006 | Huang et al. |
| 2006/0272652 A1 | 12/2006 | Stocker et al. |
| 2006/0276771 A1 | 12/2006 | Galley et al. |
| 2007/0016127 A1 | 1/2007 | Staib et al. |
| 2007/0016170 A1 | 1/2007 | Kovelman |
| 2007/0016449 A1 | 1/2007 | Cohen et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc et al. |
| 2007/0060874 A1 | 3/2007 | Nesbitt et al. |
| 2007/0066956 A1 | 3/2007 | Finkel |
| 2007/0073236 A1 | 3/2007 | Mernoe et al. |
| 2007/0083152 A1 | 4/2007 | Williams, Jr. et al. |
| 2007/0083335 A1 | 4/2007 | Moerman |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0112298 A1 | 5/2007 | Mueller, Jr. et al. |
| 2007/0112299 A1 | 5/2007 | Smit et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0156033 A1 | 7/2007 | Causey, III et al. |
| 2007/0156092 A1 | 7/2007 | Estes et al. |
| 2007/0156457 A1 | 7/2007 | Brown |
| 2007/0167905 A1 | 7/2007 | Estes et al. |
| 2007/0167912 A1 | 7/2007 | Causey et al. |
| 2007/0173712 A1 | 7/2007 | Shah et al. |
| 2007/0173762 A1 | 7/2007 | Estes et al. |
| 2007/0179355 A1 | 8/2007 | Rosen |
| 2007/0179444 A1 | 8/2007 | Causey et al. |
| 2007/0203454 A1 | 8/2007 | Shermer et al. |
| 2007/0213657 A1 | 9/2007 | Jennewine et al. |
| 2007/0233051 A1 | 10/2007 | Hohl et al. |
| 2007/0245258 A1 | 10/2007 | Ginggen et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0287985 A1 | 12/2007 | Estes et al. |
| 2007/0299389 A1 | 12/2007 | Halbert et al. |
| 2008/0004601 A1 | 1/2008 | Jennewine et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0058773 A1 | 3/2008 | John |
| 2008/0065007 A1 | 3/2008 | Peterson et al. |
| 2008/0065016 A1 | 3/2008 | Peterson et al. |
| 2008/0071209 A1 | 3/2008 | Moubayed et al. |
| 2008/0071210 A1 | 3/2008 | Moubayed et al. |
| 2008/0071217 A1 | 3/2008 | Moubayed et al. |
| 2008/0071251 A1 | 3/2008 | Moubayed et al. |
| 2008/0071580 A1 | 3/2008 | Marcus et al. |
| 2008/0076969 A1 | 3/2008 | Kraft et al. |
| 2008/0097289 A1 | 4/2008 | Steil et al. |
| 2008/0106431 A1 | 5/2008 | Blomquist |
| 2008/0114299 A1 | 5/2008 | Damgaard-Sorensen et al. |
| 2008/0132844 A1 | 6/2008 | Peterson et al. |
| 2008/0139907 A1 | 6/2008 | Rao et al. |
| 2008/0147004 A1 | 6/2008 | Mann et al. |
| 2008/0147041 A1 | 6/2008 | Kristensen |
| 2008/0147050 A1 | 6/2008 | Mann et al. |
| 2008/0154513 A1 | 6/2008 | Kovatchev et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0206799 A1 | 8/2008 | Blomquist |
| 2008/0228056 A1 | 9/2008 | Blomquist et al. |
| 2008/0249470 A1 | 10/2008 | Malave et al. |
| 2008/0255438 A1 | 10/2008 | Saidara et al. |
| 2008/0255517 A1 | 10/2008 | Nair et al. |

(56) References Cited

U.S. PATENT DOCUMENTS

| | | |
|---|---|---|
| 2008/0264024 A1 | 10/2008 | Baaken |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0294294 A1 | 11/2008 | Blomquist |
| 2008/0300534 A1 | 12/2008 | Blomquist |
| 2008/0300572 A1 | 12/2008 | Rankers et al. |
| 2008/0300651 A1 | 12/2008 | Gerber et al. |
| 2008/0306434 A1 | 12/2008 | Dobbles et al. |
| 2008/0306444 A1 | 12/2008 | Brister et al. |
| 2008/0312584 A1 | 12/2008 | Montgomery et al. |
| 2008/0312585 A1 | 12/2008 | Brukalo et al. |
| 2009/0005726 A1 | 1/2009 | Jones et al. |
| 2009/0018779 A1 | 1/2009 | Cohen et al. |
| 2009/0030733 A1 | 1/2009 | Cohen et al. |
| 2009/0036753 A1 | 2/2009 | King |
| 2009/0054475 A1 | 2/2009 | Chen et al. |
| 2009/0067989 A1 | 3/2009 | Estes et al. |
| 2009/0069745 A1 | 3/2009 | Estes et al. |
| 2009/0069749 A1 | 3/2009 | Miller et al. |
| 2009/0069787 A1 | 3/2009 | Estes et al. |
| 2009/0085768 A1 | 4/2009 | Patel et al. |
| 2009/0088731 A1 | 4/2009 | Campbell et al. |
| 2009/0093756 A1 | 4/2009 | Minaie et al. |
| 2009/0105636 A1 | 4/2009 | Hayter et al. |
| 2009/0105646 A1 | 4/2009 | Hendrixson et al. |
| 2009/0112626 A1 | 4/2009 | Talbot et al. |
| 2009/0118592 A1 | 5/2009 | Klitgaard |
| 2009/0131860 A1 | 5/2009 | Nielsen |
| 2009/0131861 A1 | 5/2009 | Braig et al. |
| 2009/0143661 A1 | 6/2009 | Taub et al. |
| 2009/0150186 A1 | 6/2009 | Cohen et al. |
| 2009/0150865 A1 | 6/2009 | Young et al. |
| 2009/0156990 A1 | 6/2009 | Wenger et al. |
| 2009/0157003 A1 | 6/2009 | Jones et al. |
| 2009/0163855 A1 | 6/2009 | Shin et al. |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba, Jr. et al. |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0212966 A1 | 8/2009 | Panduro |
| 2009/0216100 A1 | 8/2009 | Ebner et al. |
| 2009/0240193 A1 | 9/2009 | Mensinger et al. |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0270810 A1 | 10/2009 | DeBelser et al. |
| 2009/0275886 A1 | 11/2009 | Blomquist et al. |
| 2009/0275887 A1 | 11/2009 | Estes |
| 2009/0281393 A1 | 11/2009 | Smith |
| 2010/0008795 A1 | 1/2010 | DiPerna |
| 2010/0010330 A1 | 1/2010 | Rankers et al. |
| 2010/0030045 A1 | 2/2010 | Gottlieb et al. |
| 2010/0030387 A1 | 2/2010 | Sen |
| 2010/0049164 A1 | 2/2010 | Estes |
| 2010/0056993 A1 | 3/2010 | Chase |
| 2010/0057040 A1 | 3/2010 | Hayter |
| 2010/0057043 A1 | 3/2010 | Kovatchev et al. |
| 2010/0064257 A1 | 3/2010 | Buck et al. |
| 2010/0069730 A1 | 3/2010 | Bergstrom et al. |
| 2010/0081993 A1 | 4/2010 | O'Connor |
| 2010/0094110 A1 | 4/2010 | Heller et al. |
| 2010/0094251 A1 | 4/2010 | Estes |
| 2010/0095229 A1 | 4/2010 | Dixon et al. |
| 2010/0105999 A1 | 4/2010 | Dixon et al. |
| 2010/0114015 A1 | 5/2010 | Kanderian, Jr. et al. |
| 2010/0121169 A1 | 5/2010 | Petisce et al. |
| 2010/0121170 A1 | 5/2010 | Rule |
| 2010/0125241 A1 | 5/2010 | Prud'Homme et al. |
| 2010/0130933 A1 | 5/2010 | Holland et al. |
| 2010/0138197 A1 | 6/2010 | Sher |
| 2010/0145276 A1 | 6/2010 | Yodfat et al. |
| 2010/0145303 A1 | 6/2010 | Yodfat et al. |
| 2010/0156633 A1 | 6/2010 | Buck, Jr. et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0174228 A1 | 7/2010 | Buckingham et al. |
| 2010/0174266 A1 | 7/2010 | Estes |
| 2010/0174553 A1 | 7/2010 | Kaufman et al. |
| 2010/0179402 A1 | 7/2010 | Goode, Jr. et al. |
| 2010/0185142 A1 | 7/2010 | Kamen et al. |
| 2010/0185152 A1 | 7/2010 | Larsen et al. |
| 2010/0185175 A1 | 7/2010 | Kamen et al. |
| 2010/0192686 A1 | 8/2010 | Kamen et al. |
| 2010/0198034 A1 | 8/2010 | Thomas et al. |
| 2010/0198142 A1 | 8/2010 | Sloan et al. |
| 2010/0205001 A1 | 8/2010 | Knudsen et al. |
| 2010/0218132 A1 | 8/2010 | Soni et al. |
| 2010/0222765 A1 | 9/2010 | Blomquist et al. |
| 2010/0228186 A1 | 9/2010 | Estes et al. |
| 2010/0234709 A1 | 9/2010 | Say et al. |
| 2010/0235439 A1 | 9/2010 | Goodnow |
| 2010/0249530 A1 | 9/2010 | Rankers et al. |
| 2010/0249561 A1 | 9/2010 | Patek et al. |
| 2010/0261987 A1 | 10/2010 | Kamath et al. |
| 2010/0262078 A1 | 10/2010 | Blomquist |
| 2010/0262117 A1 | 10/2010 | Magni et al. |
| 2010/0262434 A1 | 10/2010 | Shaya |
| 2010/0274218 A1 | 10/2010 | Yodfat et al. |
| 2010/0274592 A1 | 10/2010 | Nitzan et al. |
| 2010/0274751 A1 | 10/2010 | Blomquist |
| 2010/0277119 A1 | 11/2010 | Montague et al. |
| 2010/0280329 A1 | 11/2010 | Randloev et al. |
| 2010/0286563 A1 | 11/2010 | Bryer et al. |
| 2010/0286601 A1 | 11/2010 | Yodfat et al. |
| 2010/0286653 A1 | 11/2010 | Kubel et al. |
| 2010/0292634 A1 | 11/2010 | Kircher, Jr. et al. |
| 2010/0295686 A1 | 11/2010 | Sloan et al. |
| 2010/0298681 A1 | 11/2010 | Say et al. |
| 2010/0298685 A1 | 11/2010 | Hayter et al. |
| 2010/0305421 A1 | 12/2010 | Ow-Wing |
| 2010/0305545 A1 | 12/2010 | Kanderian, Jr. et al. |
| 2010/0305965 A1 | 12/2010 | Benjamin et al. |
| 2010/0312085 A1 | 12/2010 | Andrews et al. |
| 2010/0324382 A1 | 12/2010 | Cantwell et al. |
| 2010/0324398 A1 | 12/2010 | Tzyy-Ping |
| 2010/0331651 A1 | 12/2010 | Groll |
| 2011/0004188 A1 | 1/2011 | Shekalim |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0015509 A1 | 1/2011 | Peyser |
| 2011/0021898 A1 | 1/2011 | Wei et al. |
| 2011/0022025 A1 | 1/2011 | Savoie et al. |
| 2011/0033833 A1 | 2/2011 | Blomquist et al. |
| 2011/0040247 A1 | 2/2011 | Mandro et al. |
| 2011/0040251 A1 | 2/2011 | Blomquist et al. |
| 2011/0047499 A1 | 2/2011 | Mandro et al. |
| 2011/0050428 A1 | 3/2011 | Istoc |
| 2011/0053121 A1 | 3/2011 | Heaton |
| 2011/0054390 A1 | 3/2011 | Searle et al. |
| 2011/0054391 A1 | 3/2011 | Ward et al. |
| 2011/0056264 A1 | 3/2011 | Kaplan et al. |
| 2011/0058485 A1 | 3/2011 | Sloan |
| 2011/0060281 A1 | 3/2011 | Aeschlimann et al. |
| 2011/0071372 A1 | 3/2011 | Sloan et al. |
| 2011/0071464 A1 | 3/2011 | Palerm |
| 2011/0071465 A1 | 3/2011 | Wang et al. |

(56) References Cited

U.S. PATENT DOCUMENTS

| | | |
|---|---|---|
| 2011/0071765 A1 | 3/2011 | Yodfat et al. |
| 2011/0077481 A1 | 3/2011 | Say et al. |
| 2011/0077963 A1 | 3/2011 | Knudsen et al. |
| 2011/0082439 A1 | 4/2011 | Wenger et al. |
| 2011/0087165 A1 | 4/2011 | Amborn et al. |
| 2011/0092788 A1 | 4/2011 | Long et al. |
| 2011/0092894 A1 | 4/2011 | McGill et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0105955 A1 | 5/2011 | Yudovsky et al. |
| 2011/0106011 A1 | 5/2011 | Cinar et al. |
| 2011/0106050 A1 | 5/2011 | Yodfat et al. |
| 2011/0112504 A1 | 5/2011 | Causey et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118662 A1 | 5/2011 | Mhatre et al. |
| 2011/0118699 A1 | 5/2011 | Yodfat et al. |
| 2011/0124996 A1 | 5/2011 | Reinke et al. |
| 2011/0124999 A1 | 5/2011 | Reggiardo et al. |
| 2011/0125085 A1 | 5/2011 | McGill et al. |
| 2011/0125095 A1 | 5/2011 | Lebel et al. |
| 2011/0126188 A1 | 5/2011 | Bernstein et al. |
| 2011/0130716 A1 | 6/2011 | Estes et al. |
| 2011/0130746 A1 | 6/2011 | Budiman |
| 2011/0133946 A1 | 6/2011 | Kopp et al. |
| 2011/0137239 A1 | 6/2011 | Debelser et al. |
| 2011/0144586 A1 | 6/2011 | Michaud et al. |
| 2011/0144616 A1 | 6/2011 | Michaud et al. |
| 2011/0152770 A1 | 6/2011 | DiPerna et al. |
| 2011/0152824 A1 | 6/2011 | DiPerna et al. |
| 2011/0160654 A1 | 6/2011 | Hanson et al. |
| 2011/0160695 A1 | 6/2011 | Sigrist et al. |
| 2011/0166544 A1 | 7/2011 | Verhoef et al. |
| 2011/0166875 A1 | 7/2011 | Hayter et al. |
| 2011/0172744 A1 | 7/2011 | Davis et al. |
| 2011/0178461 A1 | 7/2011 | Chong et al. |
| 2011/0178462 A1 | 7/2011 | Moberg et al. |
| 2011/0178717 A1 | 7/2011 | Goodnow et al. |
| 2011/0184264 A1 | 7/2011 | Galasso et al. |
| 2011/0184342 A1 | 7/2011 | Pesach et al. |
| 2011/0190701 A1 | 8/2011 | Remde et al. |
| 2011/0193704 A1 | 8/2011 | Harper et al. |
| 2011/0196213 A1 | 8/2011 | Thukral et al. |
| 2011/0202040 A1 | 8/2011 | Remde et al. |
| 2011/0205065 A1 | 8/2011 | Strachan et al. |
| 2011/0208155 A1 | 8/2011 | Palerm et al. |
| 2011/0213225 A1 | 9/2011 | Bernstein et al. |
| 2011/0213306 A1 | 9/2011 | Hanson et al. |
| 2011/0256024 A1 | 10/2011 | Cole et al. |
| 2011/0257625 A1 | 10/2011 | Jasperson et al. |
| 2011/0257895 A1 | 10/2011 | Brauker et al. |
| 2011/0266999 A1 | 11/2011 | Yodfat et al. |
| 2012/0013625 A1 | 1/2012 | Blomquist et al. |
| 2012/0013802 A1 | 1/2012 | Blomquist et al. |
| 2012/0029433 A1 | 2/2012 | Michaud et al. |
| 2012/0029941 A1 | 2/2012 | Malave et al. |
| 2012/0030610 A1 | 2/2012 | DiPerna et al. |
| 2012/0041415 A1 | 2/2012 | Estes et al. |
| 2012/0053522 A1 | 3/2012 | Yodfat et al. |
| 2012/0059353 A1 | 3/2012 | Kovatchev et al. |
| 2012/0059673 A1 | 3/2012 | Cohen et al. |
| 2012/0095315 A1 | 4/2012 | Tenbarge et al. |
| 2012/0109100 A1 | 5/2012 | Estes et al. |
| 2012/0123230 A1 | 5/2012 | Brown et al. |
| 2012/0163481 A1 | 6/2012 | Ebner et al. |
| 2012/0185267 A1 | 7/2012 | Kamen et al. |
| 2012/0191061 A1 | 7/2012 | Yodfat et al. |
| 2012/0191063 A1 | 7/2012 | Brauker et al. |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0246106 A1* | 9/2012 | Atlas .................... G16H 50/20 700/282 |
| 2012/0265722 A1 | 10/2012 | Blomquist |
| 2012/0277667 A1 | 11/2012 | Yodat et al. |
| 2012/0296269 A1 | 11/2012 | Blomquist |
| 2012/0330227 A1 | 12/2012 | Budiman et al. |
| 2013/0012917 A1 | 1/2013 | Miller et al. |
| 2013/0046281 A1 | 2/2013 | Javitt |
| 2013/0053816 A1 | 2/2013 | DiPerna et al. |
| 2013/0131630 A1 | 5/2013 | Blomquist |
| 2013/0324928 A1 | 12/2013 | Kruse |
| 2013/0331790 A1 | 12/2013 | Brown et al. |
| 2013/0345625 A1 | 12/2013 | Causey, III et al. |
| 2013/0345663 A1 | 12/2013 | Agrawal et al. |
| 2014/0005633 A1 | 1/2014 | Finan |
| 2014/0012511 A1 | 1/2014 | Mensinger et al. |
| 2014/0019396 A1 | 1/2014 | Carlsgaard et al. |
| 2014/0066890 A1 | 3/2014 | Sloan et al. |
| 2014/0074059 A1 | 3/2014 | Howell et al. |
| 2014/0137641 A1 | 5/2014 | Brown |
| 2014/0171772 A1 | 6/2014 | Blomquist |
| 2014/0180203 A1* | 6/2014 | Budiman ............ A61M 5/1723 604/66 |
| 2014/0273042 A1 | 9/2014 | Saint |
| 2014/0275419 A1 | 9/2014 | Ward et al. |
| 2014/0276419 A1 | 9/2014 | Rosinko et al. |
| 2014/0276420 A1 | 9/2014 | Rosinko |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276570 A1 | 9/2014 | Saint |
| 2014/0276574 A1 | 9/2014 | Saint |
| 2014/0350371 A1 | 11/2014 | Blomquist et al. |
| 2014/0378898 A1 | 12/2014 | Rosinko |
| 2015/0045770 A1 | 2/2015 | Debelser et al. |
| 2015/0073337 A1 | 3/2015 | Saint et al. |
| 2015/0165117 A1* | 6/2015 | Palerm ............. A61M 5/14244 604/151 |
| 2015/0182693 A1 | 7/2015 | Rosinko |
| 2015/0182695 A1 | 7/2015 | Rosinko |
| 2015/0217044 A1 | 8/2015 | Blomquist |
| 2015/0217051 A1* | 8/2015 | Mastrototaro .... A61M 5/14248 604/504 |
| 2015/0314062 A1 | 11/2015 | Blomquist et al. |
| 2016/0030669 A1 | 2/2016 | Harris et al. |
| 2016/0082188 A1 | 3/2016 | Blomquist et al. |
| 2016/0199571 A1 | 7/2016 | Rosinko et al. |
| 2016/0228041 A1 | 8/2016 | Heller et al. |
| 2017/0000943 A1 | 1/2017 | Blomquist et al. |
| 2018/0092578 A1 | 4/2018 | Blomquist |
| 2018/0133397 A1 | 5/2018 | Estes |
| 2019/0328967 A1 | 10/2019 | Blomquist et al. |
| 2019/0350501 A1 | 11/2019 | Blomquist et al. |
| 2019/0365997 A1 | 12/2019 | Harris |
| 2019/0388015 A1 | 12/2019 | Blomquist |
| 2020/0101226 A1 | 4/2020 | Blomquist et al. |
| 2020/0114076 A1 | 4/2020 | Ulrich et al. |
| 2020/0261649 A1 | 8/2020 | Michaud et al. |

FOREIGN PATENT DOCUMENTS

| | | |
|---|---|---|
| DE | 19819407 A1 | 11/1999 |
| DE | 10121317 A1 | 11/2002 |
| DE | 10352456 A1 | 7/2005 |
| EP | 1102194 A2 | 5/2001 |
| EP | 1571582 A2 | 9/2005 |
| JP | 2006034323 A | 2/2006 |
| WO | WO-0045696 A1 | 8/2000 |
| WO | WO-0074753 A1 | 12/2000 |
| WO | WO-0152727 A1 | 7/2001 |
| WO | WO-02062212 A2 | 8/2002 |
| WO | WO-03082091 A2 | 10/2003 |
| WO | WO-2005046559 A2 | 5/2005 |

(56) References Cited

FOREIGN PATENT DOCUMENTS

| | | |
|---|---|---|
| WO | WO-2006061169 A1 | 6/2006 |
| WO | WO-2006127841 A2 | 11/2006 |
| WO | WO-2007000425 A2 | 1/2007 |
| WO | WO-2007056592 A2 | 5/2007 |
| WO | WO-2007065944 A1 | 6/2007 |
| WO | WO-2007089537 A1 | 8/2007 |
| WO | WO-2007149533 A2 | 12/2007 |
| WO | WO-2008048556 A2 | 4/2008 |
| WO | WO-2008048582 A1 | 4/2008 |
| WO | WO-2008048583 A1 | 4/2008 |
| WO | WO-2008048584 A1 | 4/2008 |
| WO | WO-2008048585 A1 | 4/2008 |
| WO | WO-2008048586 A1 | 4/2008 |
| WO | WO-2008048587 A1 | 4/2008 |
| WO | WO-2008091320 A2 | 7/2008 |
| WO | WO-2008103175 A1 | 8/2008 |
| WO | WO-2008112078 A2 | 9/2008 |
| WO | WO-2008144693 A1 | 11/2008 |
| WO | WO-2008144695 A1 | 11/2008 |
| WO | WO-2008144697 A1 | 11/2008 |
| WO | WO-2008144698 A1 | 11/2008 |
| WO | WO-2008153689 A1 | 12/2008 |
| WO | WO-2008153819 A1 | 12/2008 |
| WO | WO-2009016636 A2 | 2/2009 |
| WO | WO-2009032399 A1 | 3/2009 |
| WO | WO-2009032400 A1 | 3/2009 |
| WO | WO-2009035759 A1 | 3/2009 |
| WO | WO-2009088983 A2 | 7/2009 |
| WO | WO-2009089028 A2 | 7/2009 |
| WO | WO-2009089029 A2 | 7/2009 |
| WO | WO-2010111505 A2 | 9/2010 |
| WO | WO-2011068648 A2 | 6/2011 |
| WO | WO-2013016363 A2 | 1/2013 |
| WO | WO-2013184896 A1 | 12/2013 |
| WO | WO-2018085600 A1 | 5/2018 |

OTHER PUBLICATIONS

Bott, et al., "Impact of Smoking on the Metabolic Action of Subcutaneous Regular Insulin in Type 2 Diabetic Patients," Horm. Metab. Res., vol. 37, 2005, pp. 445-449.

Chase, et at., "The Use of Insulin Pumps With Meal Bolus Alarms in Children With Type 1 Diabetes to Improve Glycemic Control," Diabetes Carem, vol. 29, No. 5, May 2006, pp. 1012-1015.

"Compare Insulin Pump for Diabetes," Printed from www.diabetesnet.com/diabetes-technology/insulin-pump-models.php, Jun. 18, 2009, 4 pages.

Lehmann, et al., "Combining rule-based reasoning and mathematical modeling in diabetes care," Artificial Intelligence in Medicine, vol. 6, 1994, pp. 137-160.

Hildebrandt P, "Subcutaneous Absorption of Insulin in Insulin-Dependent Diavetic patients. Influence of Species Physico-Chemical properties of Insulin and Physiological factors," Danish Medical Bulletin, Aug. 1991, 10 pages.

Plougmann, et al., "DiasNet—a diabetes advisory system for communication and education via the internet," International Journal of Medical Informatics, vol. 64, 2001, pp. 319-330.

Puckett, et al., "A model for multiple subcutaneous insulin injections developed from individual diabetic patient data," vol. 269, 1995, p. E1115-E1124.

Smith Medical MD Inc., "Deltec Cozmo, Personalized Insulin Pump, Starting Guide," http://web.archive.org/web/20041207133223/http://www.cozmore.com/Library/-upload/starting.sub.--guide.sub.--032004.pdf, XP002497833, Dec. 7, 2004, pp. 1-83.

Stapel E., "Converting Between Decimals, Fractions, and Percents," Purplemath, 2006, 9 pages, Available at http://www.purplemath.com/modules/percents2.htm, 2006.

Trajanoski, et al., "Pharmacokinetic Model for the Absorption of Subcutaneously Injected Soluble Insulin and Monomeric Insulin Analogues," Biomedizinische Technik, vol. 38, No. 9. Sep. 1, 1993, pp. 224-231.

Wach, et al., "Numerical Approximation of Mathematical Model for Absorption of Subcutaneously Injected Insulin," Med & Biol. Eng & comput., vol. 33, 1995, pp. 18-23.

Walsh, et al., "Diabetes Technology—Concept 1: Super Bolus," available at Diabetes Technology—Concept 1: Super Bolus available at http://www.diabetesnet.com/diabetes.sub.--technology/super.sub.--bolus.ph-p>, Sep. 17, 2007, 3 pages.

Walsh J., et al., "Select & Test Your Correction Factor," Pumping Insulin, Fourth Edition, Chapter 13, 2006, 10 Pages.

Walsh J., et al., "Select & Test Your Basal Rates," Pumping Insulin, Fourth Edition, Chapter 11, 2006, 30 pages.

Walsh J., et al., "Select and Test Your Carb Factor," Pumping Insulin, Fourth Edition, Chapter 12, 2006, 32 pages.

Walsh J., et al., "Pumping Insulin: Everything you need for Success on a Smart insulin Pump," Torrey Pines Press, San Diego, ISBN 1-884804-86-1, 2006, 3 pages.

Wikipedia.com, "Wikipedia's definition for "basal rate"," printed from wikipedia.com on Jun. 12, 2009, 1 page.

Wilinska, et al., "Insulin Kinetics in Type-1 Diabetes: Continuous and Bolus Delivery of Rapid Acting Insulin," IEEE Transactions on Biomedical Engineering, vol. 52, No. 1, Jan. 2005, pp. 3-12.

\* cited by examiner

SYSTEM AND METHOD FOR SWITCHING BETWEEN CLOSED LOOP AND OPEN LOOP CONTROL OF AN AMBULATORY INFUSION PUMP

RELATED APPLICATIONS

This application is a continuation of application Ser. No. 15/394,066 filed Dec. 29, 2016 which claims the benefit of U.S. Provisional Application No. 62/272,255 filed Dec. 29, 2015, which is hereby incorporated herein in its entirety by reference.

FIELD OF THE INVENTION

The present invention relates generally to ambulatory infusion pumps and, more particularly, to ambulatory infusion pumps that are able to safely transition from closed loop operation to open-loop operation.

BACKGROUND OF THE INVENTION

There are many applications in academic, industrial, and medical fields that benefit from devices and methods that are capable of accurately and controllably delivering fluids, such as liquids and gases that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Portable infusion pumps for delivering insulin or other medicaments can be used in conjunction with blood glucose monitoring systems, such as blood glucose meters (BGMs) and continuous glucose monitoring devices (CGMs). A CGM provides a substantially continuous estimated blood glucose level through a transcutaneous sensor that estimates blood analyte levels, such as blood glucose levels, via interrogation of the patient's interstitial fluid rather than the patient's blood. CGM systems typically consist of a transcutaneously-placed sensor, a transmitter and a monitor. A CGM system allows a patient or caregiver to insert a single sensor probe under the skin for multiple days. Thus, the patient is only required to perform a single moderately invasive action with a single entry point in the subdermal layer on, e.g., a weekly basis.

Ambulatory infusion pumps typically allow the patient or caregiver to adjust the amount of insulin or other medicament delivered, by a basal rate or a bolus, based on blood glucose data obtained by a BGM or a CGM, and in some cases include the capability to automatically adjust such medicament delivery. Some ambulatory infusion pumps may include the capability to interface with a BGM or CGM such as, e.g., by receiving measured or estimated blood glucose levels and automatically adjusting or prompting the user to adjust the level of medicament being administered or planned for administration or, in cases of abnormally low blood glucose readings, automatically temporarily ceasing or prompting the user temporarily to cease insulin administration. These portable pumps may incorporate a BGM or CGM within the hardware of the pump or may communicate with a dedicated BGM or CGM via wired or wireless data communication protocols, directly and/or via a device such as a smartphone. Such pumps may be particularly important in facilitating patient compliance and improved or more accurate treatment of diabetes. One example of integration of infusion pumps with CGM devices is described in U.S. Patent Publication No. 2014/0276419, which is hereby incorporated by reference herein.

The delivery of insulin or other medicament from a portable infusion pump making use of CGM data necessitates accurate and reliable CGM data output. Some CGM devices are calibrated with blood samples to correlate actual blood glucose data with the CGM readings. However, such calibrations are only done periodically, such as every few days or hours, such as 12 hours, and the longer it has been since a calibration event the more likely the CGM is unreliable to some degree and the more unreliable the CGM is likely to become until the next calibration.

As noted above, insulin or other medicament dosing by basal rate and/or bolus techniques could automatically be provided by a pump based on readings received into the pump from a CGM device that is, e.g., external to the portable insulin pump or integrated with the pump as a pump-CGM system in a closed-loop or semi-closed-loop fashion. With respect to insulin delivery, some systems including this feature can be referred to as artificial pancreas systems because the systems serve to mimic biological functions of the pancreas for patients with diabetes.

However, there are a number of risks in automatically dosing insulin, or other medicaments, based on CGM readings that may be inaccurate or unreliable. For example, a CGM reading or readings may indicate that a user's blood glucose level is high and therefore the pump may automatically deliver a bolus of a medicament such as insulin or increase the basal rate of a medicament such as insulin to lower the user's blood glucose to a target level. If the CGM reading inaccurately indicates that the user's blood glucose level is high, the extra insulin delivered in response may actually lower the user's blood glucose level below a desired target level, possibly to a dangerously low level. This problem may not be detected until the CGM is next calibrated, perhaps not for several hours. Thus, automatically dosing medicaments such as insulin based on CGM readings can have potentially dangerous effects in situations where the CGM readings are inaccurate or unreliable relative to the user's actual blood glucose levels. Similarly, any failure of the CGM sensor, loss of signal or communication between the CGM and the pump, other mechanical or electrical failures with the system or problems with the user's operation of the system or its components, for example, may also be dangerous to the patient.

Thus, a need exists for devices and methods that maintain safe delivery of insulin to a patient in the event of a failure of closed-loop or semi-closed-loop automatic dosing of an insulin pump.

SUMMARY OF THE INVENTION

An infusion pump system providing therapy to a patient in a closed-loop or semi-closed loop mode can safely automatically revert to open-loop therapy. The system stores a default open-loop basal rate profile in memory. The system also continually tracks the insulin on board for the patient over a plurality of closed-loop therapy intervals. When an error or event occurs requiring reversion to open-loop therapy, the system automatically provides therapy according to the open-loop basal rate profile and the tracked insulin on board amount.

In one embodiment, an infusion pump system includes a pump mechanism, a memory that stores a default open-loop basal rate profile and a communications device configured to receive information from a continuous glucose monitoring system (CGM). A processor of the system causes the pump mechanism to deliver medicament to the patient in a closed-loop manner based on the information from the CGM, while continually tracking an amount of insulin on board in the patient. When an error requiring reversion from closed-loop mode to open-loop mode is detected, the processor causes the pump mechanism to deliver medicament according to the open-loop basal rate profile stored in memory and the amount of insulin on board in the patient tracked during the closed-loop mode.

In one embodiment, an infusion pump system includes a pump mechanism and a memory that stores a default open-loop basal rate profile. A processor of the system receives information from a CGM and causes the pump mechanism to automatically deliver medicament to the patient based on therapy parameters automatically determined based on the information from the CGM while continually tracking an amount of insulin on board in the patient. When an error pertaining to the CGM occurs, the pump mechanism ceases automatically delivering medicament based on the determined therapy parameters and delivers medicament according to the open-loop basal rate profile stored in memory and the tracked amount of insulin on board in the patient.

In some embodiments, the default open-loop basal rate profile is continually updated. The closed-loop therapy can be provided over a plurality of time intervals. The insulin on board can be tracked for each time interval. The open-loop basal rate profile can be updated after each time interval based on the respective tracked insulin on board amount.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which.

Figure 1:
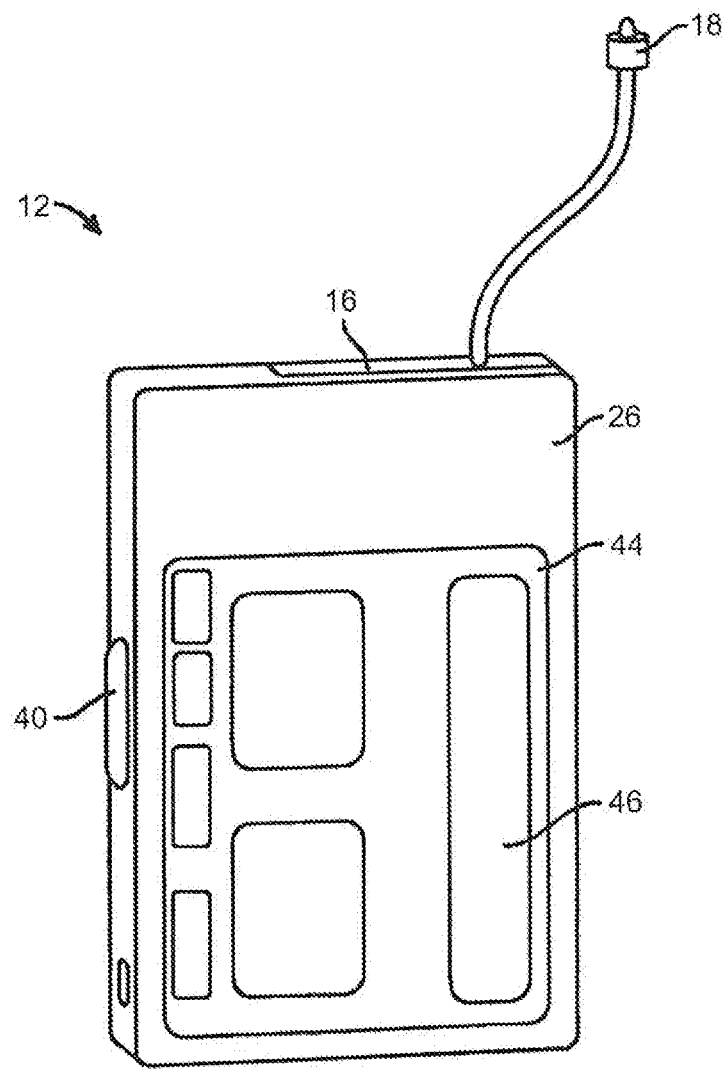
FIG. 1 is a medical device that can be used with embodiments of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an embodiment of a medical device that can be used with embodiments of the present invention. In this embodiment, the medical device is configured as a pump 12, such as an infusion pump, that can include a pumping or delivery mechanism and reservoir for delivering medicament to a patient and an output/display 44. The type of output/display 44 may vary as may be useful for a particular application. When output/display 44 is of the visual type, it may comprise an LCD display, LED display, plasma display, graphene-based display, OLED display or the like. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

Such one or more other display devices may be configured to be used in place of output/display 44 or to work in connection with output/display 44 such that information may be repeated in exact or similar fashion between output/display 44 and one or more other displays, such that different information may be repeated between/among output/display 44 and one or more other display devices, or such that information is presented solely on one or more other display devices. Such one or more other display devices may also include the capability to allow a user to input information and/or commands for operation of the infusion pump, such as, e.g., via a touchscreen, microphone, keyboard or other input devices as are known in the art.

In one embodiment, the medical device can be a portable insulin pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient. In a further embodiment, the medical device can be a glucose meter such as a BGM or CGM. Further detail regarding such systems and definitions of related terms can be found in, e.g., U.S. Pat. Nos. 8,311,749, 7,711,402 and 7,497,827, each of which is hereby incorporated by reference herein in its entirety. In other embodiments, the medical device can monitor other physiological parameters of a patient.

Figure 2:
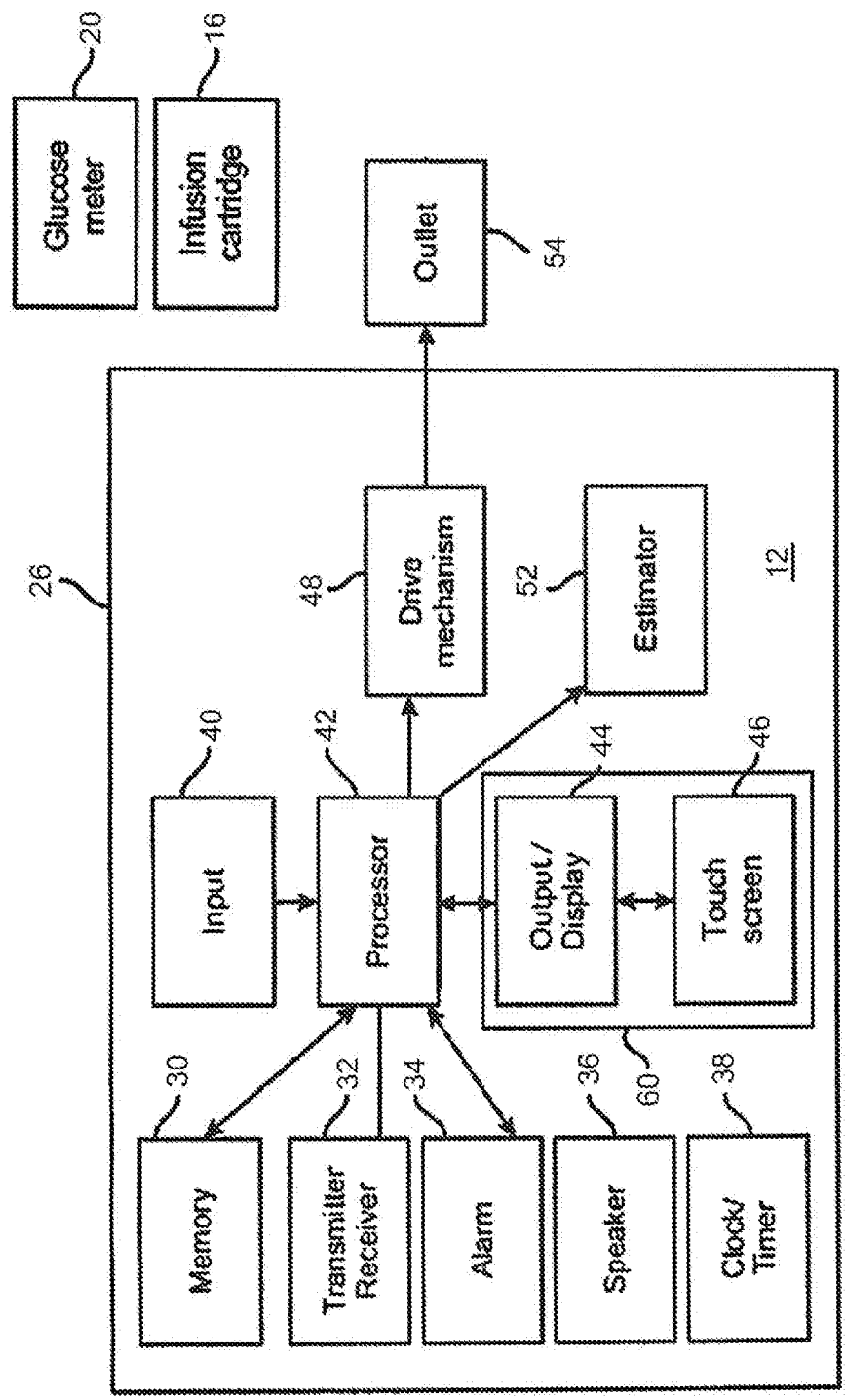
FIG. 2 is a block diagram representing a medical device that can be used with embodiments of the present invention.

FIG. 2 illustrates a block diagram of some of the features that can be used with embodiments of the present invention, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters.

Figure 3:
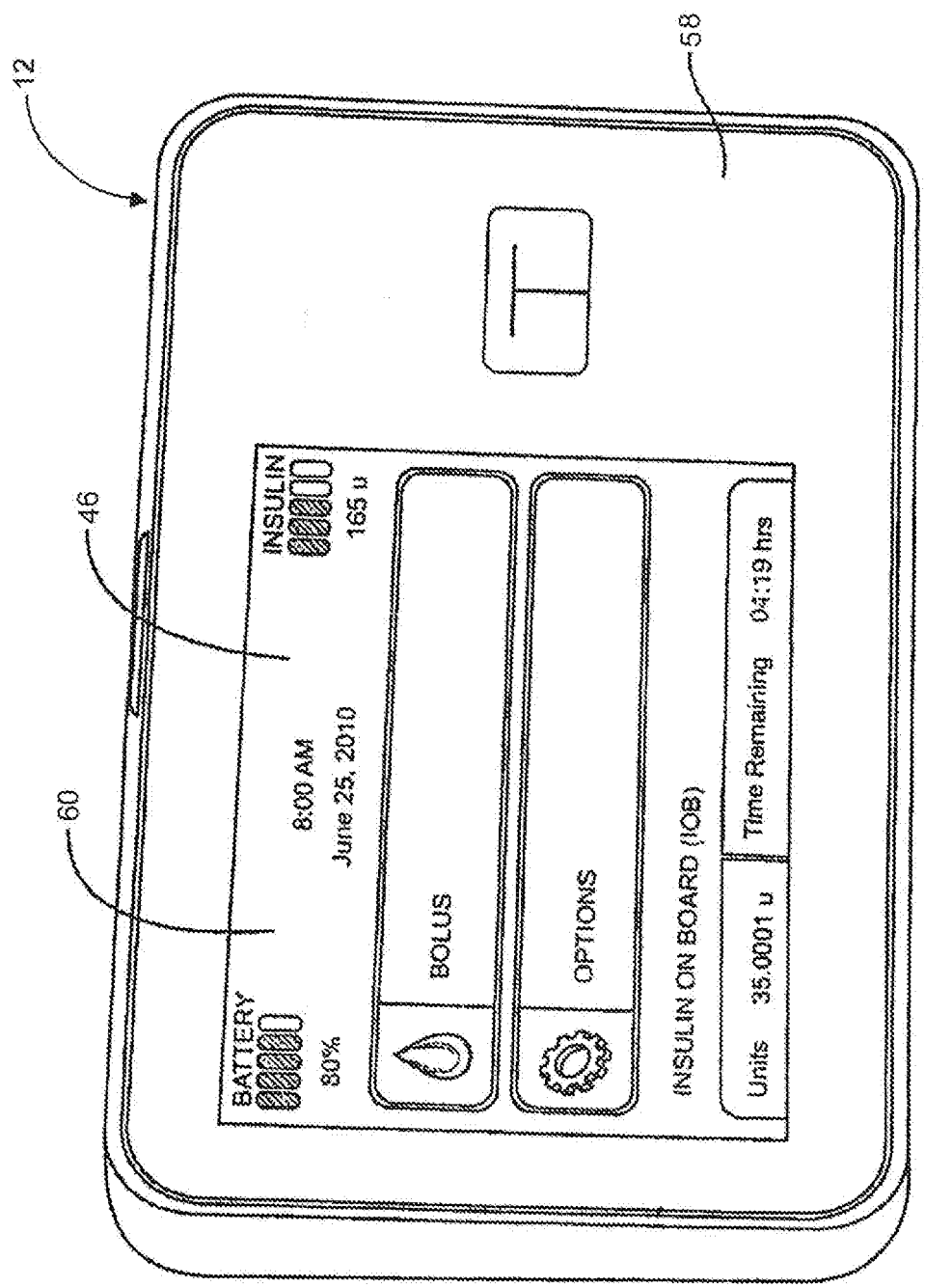
FIG. 3 depicts an exemplary screen shot of a home screen page of a user interface for use with an infusion pump system that can be used with embodiments of the present invention.

Referring to FIG. 3, a front view of pump 12 is depicted. Pump 12 may include a user interface, such as, for example, a GUI 60 on a front surface 58 or other location of pump 12. GUI 60 may include a touch-sensitive screen 46 that may be configured for displaying data, facilitating data and/or command entry, providing visual tutorials, as well as other interface features that may be useful to a caregiver or to the patient operating pump 12. The GUI can also present alarms or alerts to the user. Although described with respect to infusion pump 12, such a GUI 60 could additionally or alternatively be employed on any other device employed as part of an infusion pump system such as, for example, a CGM (described below), dedicated remote controller, smartphone, electronic tablet, computer, etc.

Figure 4:
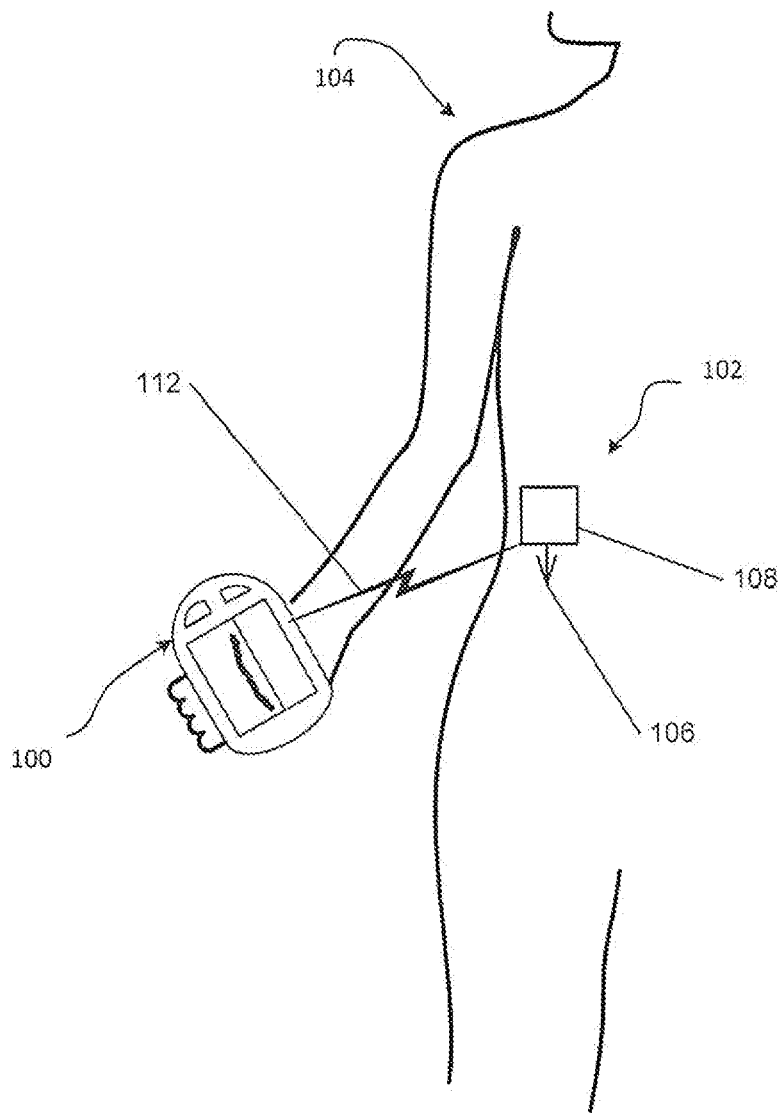
FIG. 4 is a schematic representation of a system according to embodiments of the present invention.

Pump 12 can interface directly or indirectly (via, e.g., a smartphone or other device) with a glucose meter, such as a blood glucose meter (BGM) or a continuous glucose monitor (CGM); the latter category of which provides a substantially continuous estimated blood glucose level through a transcutaneous sensor that estimates blood analyte levels, such as blood glucose levels, via interrogation of the patient's interstitial fluid rather than the patient's blood. Referring to FIG. 4, an exemplary CGM system 100 according to an embodiment of the present invention is shown (other CGM systems can be used). The illustrated CGM system includes a sensor 102 affixed to a patient 104 and can be associated with the insulin infusion device 12 in a CGM-pump system. The sensor 102 includes a sensor probe 106 configured to be inserted to a point below the dermal layer (skin) of the patient 104. The sensor probe 106 is therefore exposed to the patient's interstitial fluid or plasma beneath the skin and reacts with that interstitial fluid to produce a signal that can be associated with the patient's blood glucose (BG) level. The sensor 102 includes a sensor body 108 that transmits data associated with the interstitial fluid to which the sensor probe 106 is exposed. The data may be transmitted from the sensor 102 to the glucose monitoring system receiver 100 via a wireless transmitter, such as a near field communication (NFC) radio frequency (RF) transmitter or a transmitter operating according to a "Wi-Fi" or Bluetooth® protocol, Bluetooth® low energy protocol or the like, or the data may be transmitted via a wire connector from the sensor 102 to the monitoring system 100. Transmission of sensor data to the glucose monitoring system receiver by wireless or wired connection is represented in FIG. 4 by the arrow line 112. Further detail regarding such systems and definitions of related terms can be found in, e.g., U.S. Pat. Nos. 8,311,749, 7,711,402 and 7,497,827, each of which is hereby incorporated by reference in its entirety.

In one embodiment of a pump-CGM system, part of the CGM system 100 is incorporated into the housing of the pump 12 such that the processor 42 of the pump 12 is adapted to receive the data directly from the sensor 102 through a wired or wireless link and process and display the data on the pump display 44. In another embodiment, the CGM 100 is a separate device that communicates with the pump 12 processor 42 through a wired or wireless link to transmit processed CGM data to the pump 12 for display on the pump display 44. In further embodiments, the CGM system can transmit data to an intermediary device, such as, for example, a smartphone or dedicated remote controller that can then communicate the data to the pump.

In an embodiment of a pump-CGM system having a pump 12 that communicates with a CGM and that integrates CGM data and pump data as described herein, the CGM can automatically transmit the glucose data to the pump. The pump can then automatically determine therapy parameters and deliver medicament based on the data. For example, if the CGM data indicates that the user's blood glucose level is over a high blood glucose threshold level stored in memory, the pump can automatically calculate and deliver an insulin bolus amount and/or an increase to a user's basal rate to bring the user's blood glucose level below the threshold and/or to a target value. As with other parameters related to therapy, such thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

In one embodiment, such an automatic pump-CGM system for insulin delivery is referred to as an artificial pancreas system that provides closed-loop therapy to the patient to approximate or even mimic the natural functions of a healthy pancreas. In such a system, insulin doses are calculated based on the CGM readings (that may or may not be automatically transmitted to the pump) and are automatically delivered to the patient at least in part based on the CGM reading(s). For example, if the CGM indicates that the user has a high blood glucose level or hyperglycemia, the system can automatically calculate an insulin dose necessary to reduce the user's blood glucose level below a threshold level or to a target level and automatically deliver the dose. Alternatively, the system can automatically suggest a change in therapy upon receiving the CGM data such as an increased insulin basal rate or delivery of a bolus, but can require the user to accept the suggested change prior to delivery rather than automatically delivering the therapy adjustments.

If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the user, e.g., ingest carbohydrates and/or take other actions and/or make other suggestions as may be appropriate to address the hypoglycemic condition, singly or in any desired combination or sequence. Such determination can be made by the infusion pump providing therapy or by a separate device that transmits therapy parameters to the infusion pump. In some embodiments, multiple medicaments can be employed in such a system as, for example, a first medicament, e.g., insulin, that lowers blood glucose levels and a second medicament, e.g., glucagon, that raises blood glucose levels.

Because such artificial pancreas systems that incorporate CGM data automatically to adjust insulin therapy in a closed-loop fashion rely on the CGM data to be sufficiently accurate, it may be desirable to implement various features to, e.g., ensure the safety of the patient. Embodiments of the present invention therefore incorporate a temporary suspend feature for artificial pancreas and any other systems that provide closed-loop or semi-closed-loop therapy in which CGM data is relied upon, in whole or in part, automatically to determine dosing information. Semi-closed-loop therapy can include systems that provide some functions on an automatic, closed-loop basis and other functions on a manual or open-loop basis. For example, a system could automatically adjust basal delivery in a closed-loop mode as discussed above while still providing for manual administration of boluses. A system such as that described previously (that automatically suggests a change in therapy upon receiving CGM data such as an increased insulin basal rate or delivery of a bolus, but that requires the user to accept the suggested change prior to delivery rather than automatically delivering the therapy adjustments) could also be considered as providing semi-closed-loop therapy.

During operation of pump 12 in closed-loop mode, it may be desirable to revert to a conventional open-loop delivery mode under certain circumstances. Such circumstances may include, for example, a calibration error with sensor 102, a failure of sensor 102, a loss of signal between sensor 102 and glucose monitoring system 100, a loss of signal between glucose monitoring system 100 and pump 12, a failure of a user to replace a CGM sensor within the recommended expiration period (e.g., a number of days) such that the CGM sensor has lost adequate accuracy, a failure to calibrate a sensor properly, a failure to calibrate a sensor within a time interval, including a manufacturer's recommended time interval, or any other errors which may affect the accuracy of insulin delivery and/or patient safety.

In order for pump 12 safely to revert to open-loop operation mode, a basal rate profile for the patient should be known and the amount of insulin on board (JOB) in the patient at the time of transition between closed-loop and open-loop should be known. Pump 12 therefore includes a default open-loop basal rate profile 202, optionally stored within memory device 30 or optionally stored elsewhere and accessible by pump 12. In one embodiment, default open-loop basal rate profile 202 is programmed into pump 12 prior to patient use. Optionally, the open-loop basal rate profile may be updated during pump operation, such as at the conclusion of an operating interval 230 as described more fully below, to create an updated open-loop basal rate profile 203.

To determine the amount of IOB during closed-loop operation, pump 12, or other device monitoring the therapy, may continually track the amount of insulin delivered 210 over a period of time, such as an interval 230. Interval 230 may comprise a period of time such as hourly, daily, weekly, or other. In one embodiment, an amount of IOB 220 is calculated by comparing the amount of insulin delivered 210 over interval 230 to default open-loop basal rate profile 202. In another embodiment, the amount of IOB 220 is calculated by comparing the amount of insulin delivered 210 over interval 230 to an updated open-loop basal rate profile 203. In either embodiment, IOB 220 represents the difference between the amount of insulin actually delivered to the patient and a default basal rate. In various embodiments, the system can continually track IOB during closed-loop and/or open-loop operation, that is, repeatedly but with breaks/intervals in between where IOB is not tracked, or can continuously track IOB during closed-loop and/or open-loop operation, that is, constant tracking throughout system operation without interruption.

Optionally, the calculation of IOB 220 may take into account an IOB from one or more previous intervals. For example, if at the beginning of an interval 230, the patient already has a positive IOB value, that value will decrease over interval 230 according to known insulin pharmacokinetic models. The calculated decay of insulin already within the patient over interval 230 may be added to the IOB 220 determined as described above.

In embodiments utilizing updated open-loop basal rate profile 203, pump processor or other device may update profile 203 at the conclusion of an interval 230 as needed. For example, if IOB 220 is outside of a predetermined acceptable range, pump 12 may set updated open-loop basal rate profile 203 to correspond to the amount of insulin delivered 210 over the previous interval 230. In another embodiment, pump 12 may compare profile 203, amount of insulin delivered 210 and/or IOB 220 to determine and set a new updated open-loop basal rate profile 203. In some embodiments, when the actual basal insulin delivered 210 is less than the open-loop basal rate profile 203, the IOB 220 calculated during the interval 230 is not used to update the profile 203, or, alternatively, may be used as a negative contribution to reduce the open-loop basal rate profile 203.

During operation of pump 12 in closed-loop mode, upon occurrence of an event that requires reversion to open-loop mode to maintain patient safety, one of basal rate profiles 202 or 203 may be used along with IOB 220 to easily and safely transition to open-loop operation. Although primarily described herein as pump 12 processor 42 receiving CGM data, calculating therapy parameters, tracking JOB, storing and updating open-loop basal profiles, determining whether therapy should revert to open-loop, etc., in various embodiments a processor of any other device operated as a part of an infusion pump system could provide some or all of these functions. Examples of such devices include for example, a CGM, a smartphone, a dedicated remote controller, an electronic tablet, a computer, etc.

Figure 5:
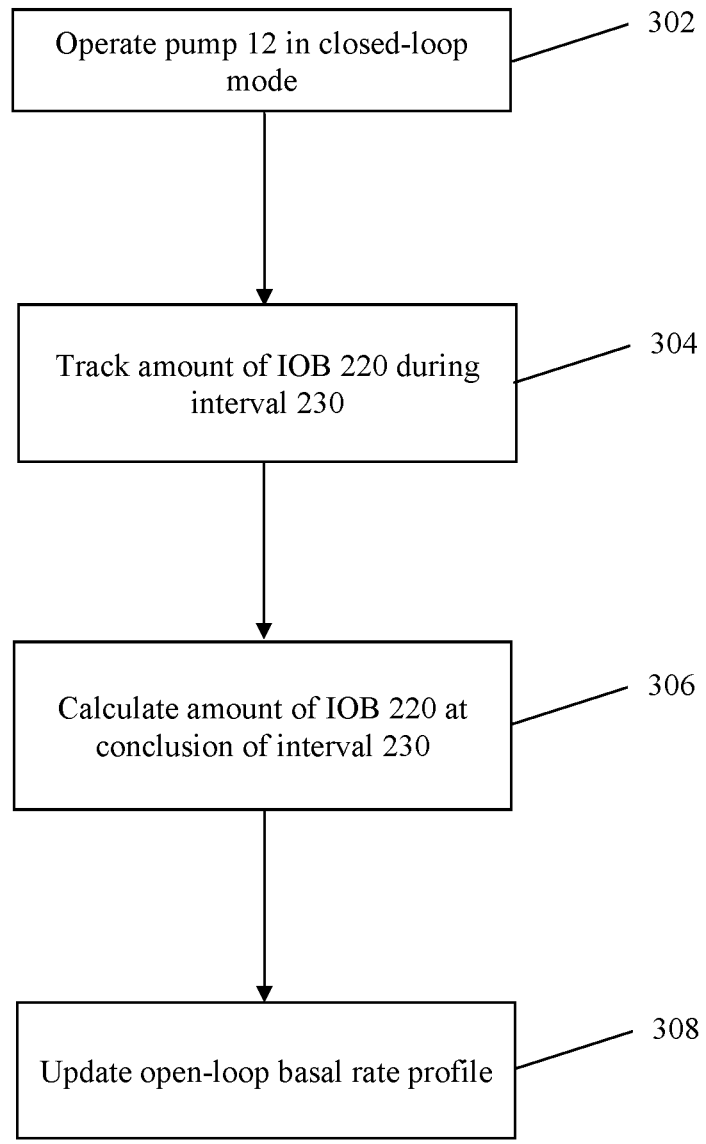
FIG. 5 is a flowchart of a method of operating a pump in a closed-loop mode according to an embodiment of the present invention.

Referring now to FIG. 5, an operational flowchart for pump/processor in closed-loop mode is depicted. At step 302, pump 12 begins operating in closed-loop mode according to an algorithm stored in memory 30 or stored in a separate location and accessible by pump 12. At step 304, the amount of IOB 220 is continually tracked during operation of pump 12 over an interval 230. At step 306, upon the conclusion of interval 230 the amount of JOB 220 is calculated and stored as described herein. At step 308, the open-loop basal rate profile 202 or 203 is updated and stored in memory 30 or stored in a separate location and accessible by pump 12 as described herein.

Figure 6:
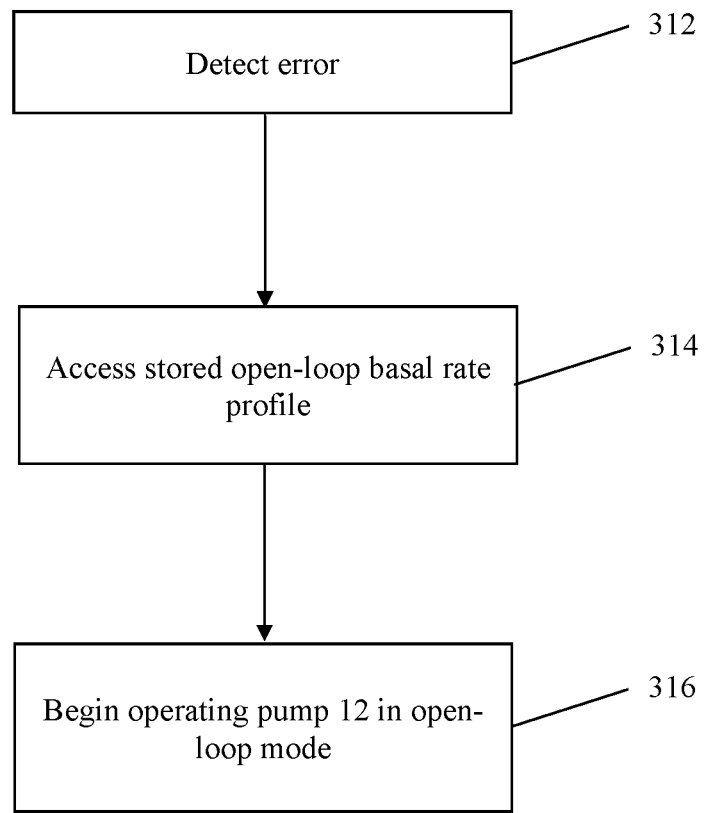
FIG. 6 is a flowchart of a method of reverting to open-loop mode according to an embodiment of the present invention.

Referring now to FIG. 6, an operational flowchart is depicted upon detection of an error. Such error may include a calibration error with sensor 102 (including, e.g., failure to calibrate the sensor within a time interval, such as a manufacturer's recommended time interval), a failure of sensor 102, an expiration of sensor 102, a loss of signal between sensor 102 and glucose monitoring system 100, a loss of signal between glucose monitoring system 100 and pump 12, or any other errors that may affect the accuracy and safety of delivery of insulin to the patient. Such error may occur at any time during operation of pump 12 in closed-loop mode. At step 314, the open-loop basal rate profile stored in step 308 is accessed. At step 316, pump 12 switches from closed-loop to open-loop operation based at least in part on the amount of IOB calculated in step 306 and/or the open-loop basal rate profile stored in step 308.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421 8,448,824; 8,573,027; 8,650,937; 8,986,523; 9,173,998; 9,180,242; 9,180,243; 9,238,100; 9,242,043; 9,335,910; 9,381,297; 9,421,329; 9,486,171; 9,486,571; 9,492,608; and 9,503,526 commonly owned U.S. Patent Publication Nos. 2009/0287180; 2012/0123230; 2013/0053816; 2013/0324928; 2013/0332874; 2014/0276419; 2014/0276420; 2014/0276423; 2014/0276531; 2014/0276553; 2014/0276556 2014/0276569; 2014/0276570; 2014/0378898; 2015/0073337; 2015/0072613; 2015/0182693; 2015/0182695; 2016/0030669; 2016/0082188; and 2016/0339172 and commonly owned U.S. patent application Ser. Nos. 14/707,851; 15/241,257 and 15/354,495 and commonly owned U.S. Provisional Application Ser. Nos. 61/911,576; 61/920,902; 61/920,914; 61/920,940; 62/139,275; 62/272, 255; 62/300,410; 62/352,164; 62/365,167; and 62/394,806.

Further incorporated by reference herein in their entirety are U.S. Pat. Nos. 8,601,465; 8,502,662; 8,452,953; 8,451, 230; 8,449,523; 8,444,595; 8,343,092; 8,285,328; 8,126, 728; 8,117,481; 8,095,123; 7,999,674; 7,819,843; 7,782, 192; 7,109,878; 6,997,920; 6,979,326; 6,936,029; 6,872, 200; 6,813,519; 6,641,533; 6,554,798; 6,551,276; 6,295, 506; and 5,665,065.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A method of providing diabetes therapy to a patient, comprising:
    delivering medicament to the patient with an infusion pump in a closed-loop mode in which therapy parameters are automatically determined and medicament is automatically delivered according to the therapy parameters based on information from a continuous glucose monitoring system;
    continually tracking an amount of insulin on board in the patient during the closed-loop mode;
    detecting that an error has occurred, the error requiring reversion from the closed-loop mode to an open-loop mode; and
    causing the infusion pump to begin to deliver the medicament to the patient in the open-loop mode in amounts according to an open-loop basal rate profile stored in memory and the amount of insulin on board in the patient in response to detection of the error.

2. The method of claim 1, wherein delivering medicament to the patient in the closed-loop mode includes delivering in the closed-loop mode for a plurality of time intervals and continually tracking the amount of insulin on board includes tracking the amount of insulin on board over a first time interval, and
    further comprising modifying the open-loop basal rate profile stored in memory after the first time interval based on the tracked amount of insulin on board over the first time interval.

3. The method of claim 2, wherein continually tracking the amount of insulin on board includes tracking the amount of insulin on board for each subsequent time interval after the first time interval, and
    further comprising modifying the open-loop basal rate profile stored in memory after each of the subsequent time intervals based on the tracked amount of insulin on board over each of the respective subsequent time intervals.

4. The method of claim 1, wherein detecting that the error has occurred includes detecting an error selected from the set consisting of: a calibration error of a sensor of the continuous glucose monitoring system, a failure to calibrate the sensor within a calibration time interval, a failure of the sensor, an expiration of the sensor, a loss of signal between the sensor and the continuous glucose monitoring system, a loss of signal with sensor, and a loss of signal with the continuous glucose monitoring system.

5. The method of claim 1, further comprising determining the therapy parameters for the closed-loop mode.

6. The method of claim 1, further comprising receiving the therapy parameters for the closed-loop mode from a separate device.

7. The method of claim 1, further comprising receiving the information from the continuous glucose monitoring system directly from a sensor of the continuous glucose monitoring system.

8. The method of claim 1, further comprising receiving the information from the continuous glucose monitoring system from a continuous glucose monitor receiver of the continuous glucose monitoring system.

9. The method of claim 1, further comprising calculating the amount of insulin on board based on a difference between an amount of insulin delivered to the patient over a time interval during the closed-loop mode and an amount of insulin in the open-loop basal rate profile over the time interval.

10. A method of providing diabetes therapy to a patient, comprising:
  receiving information from a continuous glucose monitoring system;
  causing an infusion pump to automatically deliver medicament to the patient based on therapy parameters automatically determined based on the information from the continuous glucose monitoring system;
  continually tracking an amount of insulin on board in the patient while automatically delivering the medicament based on the therapy parameters;
  detecting an error pertaining to the continuous glucose monitoring system; and
  causing the infusion pump to cease automatically delivering the medicament based on the therapy parameters automatically determined based on the information from the continuous glucose monitoring system and to begin to deliver the medicament in amounts according to an open-loop basal rate profile stored in memory and the amount of insulin on board in the patient in response to detection of the error.

11. The method of claim 10, wherein causing the infusion pump to automatically deliver medicament to the patient includes automatically delivering medicament to the patient for a plurality of time intervals and continually tracking the amount of insulin on board includes tracking the amount of insulin on board over a first time interval, and
  further comprising modifying the open-loop basal rate profile stored in memory after the first time interval based on the tracked amount of insulin on board over the first time interval.

12. The method of claim 11, wherein continually tracking the amount of insulin on board includes tracking the amount of insulin on board for each subsequent time interval after the first time interval, and
  further comprising modifying the open-loop basal rate profile stored in memory after each of the subsequent time intervals based on the tracked amount of insulin on board over each of the respective subsequent time intervals.

13. The method of claim 10, wherein detecting the error pertaining to the continuous glucose monitoring system includes detecting an error selected from the set consisting of: a calibration error of a sensor of the continuous glucose monitoring system, a failure to calibrate the sensor within a calibration time interval, a failure of the sensor, an expiration of the sensor, a loss of signal with the sensor and a loss of signal with the continuous glucose monitoring system.

14. The method of claim 10, further comprising determining the therapy parameters.

15. The method of claim 10, further comprising receiving the therapy parameters from a separate device.

16. The method of claim 10, wherein receiving the information from the continuous glucose monitoring system includes receiving the information directly from a sensor of the continuous glucose monitoring system.

17. The method of claim 10, wherein receiving the information from the continuous glucose monitoring system includes receiving the information from a continuous glucose monitor receiver of the continuous glucose monitoring system.

18. The method of claim 10, further comprising calculating the amount of insulin on board based on a difference between an amount of insulin delivered to the patient over a time interval when medicament is automatically delivered according to the therapy parameters and an amount of insulin in the open-loop basal rate profile over the time interval.

19. A method of providing diabetes therapy to a patient, comprising:
  causing an infusion pump to deliver medicament to the patient in a closed-loop mode in which therapy parameters are automatically determined and medicament is automatically delivered according to the therapy parameters based on estimated blood glucose levels;
  continually tracking an amount of insulin on board in the patient during the closed-loop mode;
  detecting that an error has occurred, the error requiring reversion from the closed-loop mode to an open-loop mode; and
  causing the infusion pump to begin to deliver the medicament to the patient in the open-loop mode in amounts according to an open-loop basal rate profile and the amount of insulin on board in the patient in response to detection of the error.

20. The method of claim 19, further comprising calculating the amount of insulin on board based on a difference between an amount of insulin delivered to the patient over a time interval when medicament is automatically delivered according to the therapy parameters and an amount of insulin in the open-loop basal rate profile over the time interval.

* * * * *